United States Patent [19]

Fuller et al.

[11] Patent Number: 5,508,203
[45] Date of Patent: Apr. 16, 1996

[54] APPARATUS AND METHOD FOR RADIO FREQUENCY SPECTROSCOPY USING SPECTRAL ANALYSIS

[76] Inventors: Milton E. Fuller, 500 Winchester Dr., Reno, Nev. 89506; Frank J. Cherne, 1295 Wesley Dr., Reno, Nev. 89503

[21] Appl. No.: 103,410

[22] Filed: Aug. 6, 1993

[51] Int. Cl.$^6$ .......................... G01N 27/00; G01N 33/50
[52] U.S. Cl. ................ 436/149; 128/665; 324/642; 422/82.01; 436/79; 436/94; 436/95; 436/131; 436/108; 436/150; 436/806
[58] Field of Search ...................... 324/642, 643, 324/644, 645, 646; 128/633, 664, 665, 666, 635; 422/82.01, 82.02; 436/94, 95, 79, 108, 149, 150, 151, 806, 131; 73/53.01

[56] References Cited

U.S. PATENT DOCUMENTS

| | | | |
|---|---|---|---|
| 3,238,451 | 3/1966 | Shively | 324/646 |
| 4,407,290 | 10/1983 | Wilbur | 128/633 |
| 4,510,437 | 4/1985 | Iskander | 324/642 X |
| 4,679,426 | 7/1987 | Fuller et al. | 73/53.01 |
| 4,765,179 | 8/1988 | Fuller et al. | 73/53.01 |
| 4,812,738 | 3/1989 | Itaya et al. | 324/642 X |
| 4,880,014 | 11/1989 | Zarowitz et al. | 128/734 |
| 5,072,189 | 12/1991 | Openlander | 324/646 X |
| 5,077,476 | 12/1991 | Rosenthal | 250/341 |
| 5,103,181 | 4/1992 | Gaisford et al. | 324/642 X |
| 5,120,648 | 6/1992 | Lim et al. | 435/173.2 |
| 5,142,612 | 8/1992 | Sheirik | 395/11 |
| 5,144,224 | 9/1992 | Larsen | 324/631 X |
| 5,233,306 | 8/1993 | Misra | 324/642 X |

OTHER PUBLICATIONS

Zumdahl *Chemistry*, 1986, p. 238.
Serway, *Physics, for Scientists and Engineers/with Modern Physics*, 1983, pp. 756–757.

*Primary Examiner*—Robert J. Warden
*Assistant Examiner*—Robert Carpenter

[57] ABSTRACT

A source of high frequency electromagnetic radiation is coupled to a specimen containing a target chemical whose presence and/or concentration is to be ascertained. Preferably the source radiation includes a plurality of high frequency spectra, at least one of which encourages energy transfer with the chemical of interest. The source radiation is coupled to the specimen via a probe pair that is also used to access a return signal representing an interaction between the source signal and the specimen. The return signal is processed to yield a spectral signature correlating to the target chemical and/or its concentration. Preferably signal processing compares frequency spectra within the source signal to spectra within a sampled return signal. The sampled return signal is a signal obtained by sampling a return signal at the probe pair and by sampling the response to the source signal of a circuit that electrically approximates the specimen. The amplitude and/or phase difference between the sampled return signal and the source signal provides recognition of the spectral signature. Target chemical concentration data may be obtained from the signature and can be displayed in a number of ways. Operation of the signal processor may be optimized using a neural network. In the preferred embodiment, the specimen is a human finger that is pressed against the probe pair, and the chemical is glucose. The invention thus permits a lay user to non-invasively determine his or her glucose level.

32 Claims, 5 Drawing Sheets

APPARATUS AND METHOD FOR RADIO FREQUENCY SPECTROSCOPY USING SPECTRAL ANALYSIS

FIELD OF THE INVENTION

This invention relates generally to radio frequency spectroscopy, and more particularly to spectral analysis of a source electromagnetic signal coupled to a specimen to determine the presence and/or concentration of a chemical within the specimen.

BACKGROUND OF THE INVENTION

Many conventional analysis techniques measure the concentration of a chemical in a test specimen or sample, even where the specimen contains a complex mixture of chemicals. Such techniques include mass spectrophotometry, nuclear resonance, flame photometry, conductance and refractometry. While these techniques work, unfortunately, their accuracy is too often directly related to their cost. Further, many such techniques alter or destroy the specimen under test, and require relatively elaborate equipment.

More recently attempts have been made to determine various properties of materials, using sound, electromagnetic waves, or single pulses as the basis for analysis. In contrast to conventional chemical analysis, wave and pulse-based techniques can provide a non-invasive in vivo analysis.

For example, U.S. Pat. No. 4,679,426 (Jul. 1987), assigned to assignee herein, discloses a non-invasive in vivo technique for measuring concentration of chemicals, sodium chloride for example. Periodic electromagnetic waves having a repetition rate of about 10 MHz to 100 MHz were coupled to a subject's finger, and sodium or chloride ions within the finger apparently distorted these waves. This distortion in the composite waveform was received from the finger, using the same electrode-antenna pair used to couple the waves to the finger. The composite waveform distortion was then examined, and found to provide meaningful data as to chemical concentrations.

Glucose is an especially important chemical, a knowledge of whose absolute concentration level can be vital to diabetics. Several techniques for providing blood-sugar analysis are known, which permit subjects to determine their own glucose levels. Unfortunately many such techniques require invasive sampling of the subject.

One non-invasive technique for determining glucose levels in vivo was disclosed in U.S. Pat. No. 4,765,179 (Aug. 1988), also assigned to assignee herein. A periodic train of electromagnetic energy, preferably having a repetition rate of about 1 MHz to 1 GHz, was coupled to a subject's finger. The composite waveform distortion was then analyzed and found to provide meaningful analysis of glucose levels in the range of about 50 to 150 mg percent. However, beyond about 110 mg percent, it was desirable to fine-tune the electromagnetic energy to maintain measurement accuracy.

Understandably, glucose is a complex chemical. Monitoring the concentration of glucose in blood presents substantial challenges to discriminate against other materials in the blood that may mask or alter the analysis results.

What is needed is a non-invasive in vivo apparatus and method for determining a chemical level in a subject, including the chemical glucose. Preferably a lay person should be able to determine the chemical level, for example a diabetic determining his or her own glucose level. The present invention provides such apparatus and method.

SUMMARY OF THE INVENTION

A source of electromagnetic signals having many high frequency components is coupled via a probe pair to a sample that may include a target chemical. Certain chemicals under test within the sample seem to cause energy transfer or energy redistribution of certain spectra of the source signal. The result is that a return signal, present at the probe pair, can have spectra with different energy levels than were present in the source signal. For example, some harmonic frequencies of the transmitted source signal may be returned attenuated or even amplified, probably due to certain non-linear dielectric processes occurring within the sample.

In the preferred embodiment, the source signal is preferably a high frequency pulse train that is rich in harmonics, for example a 30 MHz square-wave having nanosecond transition times that generates a comb spectra. However a source of fewer frequencies or multiple sources of separate frequencies, which frequencies are not necessarily harmonically related, could also be used.

In the preferred embodiment, the specimen is human tissue, preferably a finger that is pressed against a probe pair, and the target chemical is glucose in the blood within the finger.

The return signal is sampled via the probe pair, and frequency spectra therein are processed within a signal processor. The signal processor can recognize the spectral signature associated with certain target chemicals within the specimen, and provides data as to the presence and concentration of such chemicals.

Within the signal processor, the response of the specimen to the source signal (e.g., the return signal at the probe pair) preferably is switchably sampled with the response of a specimen equivalent circuit to the source signal to provide a sampled return signal. Ideally, the return signal from the equivalent circuit would be the same as that from the specimen, assuming that no abnormal levels of target chemicals were present in the specimen. Sampling in this fashion helps minimize error due to drift of components within the signal processor system.

A synthesized local oscillator preferably is phase locked to the source signal and, under microprocessor control, generates a mixer oscillator. The mixer oscillator control signal is offset by an intermediate frequency from a return signal harmonic of interest.

The source signal and sampled return signal are passed through band pass filter banks that switchably pass bands of spectra within each signal. Signals within these frequency bands are mixed with the synthesized mixer output signal to produce a pair of signals at an intermediate frequency ("IF"). The IF is the frequency difference between the specific return signal harmonic of interest and the microprocessor-controlled synthesized mixer oscillator signal.

The source and sampled return signals pass through the intermediate frequency stages to provide signal phase shift and amplitude information to a microprocessor within the digital signal processing system. By suitably correlating spectral components of the sampled return signal, the signal processing system can recognize a spectral signature associated with a target chemical within the specimen. Characteristics of different spectral signatures can provide meaningful data as to the presence and concentration of one or more target chemicals within the specimen.

Sampled return signals can experience variation due to temperature and probe pair pressure against specimen tissue. To account for such variation, the signal processor microprocessor receives the source frequency fundamental response from the probe pair as well as the source frequency fundamental response from a calibrated circuit equivalent to the specimen tissue.

The system microprocessor provides output that may be displayed in a spectrum analyzer format, or in a textual or graphical format to be read by a user from a display monitor or printer. If desired, the system output may simply be a "GO/NO GO" indicator, indicating for example that an upper level of glucose concentration has been exceeded, or a calibrated output meter. A user self-testing with the present invention would know from such output indicators to take insulin immediately.

Enhanced specificity of the present invention to a desired chemical within the sample is obtained by tailoring the spectral components of the source signals, and by tailoring the received spectra to be signal processed. Within the sample, different components and components of differing concentration may be recognized by the spectral signature associated with the received signal.

An alternative embodiment provides a signal processing system that includes a neural network that is self-optimizing to recognize the spectral signature associated with absolute glucose concentration levels. Other features and advantages of the invention will appear from the following description in which the preferred embodiments have been set forth in detail, in conjunction with the accompanying drawings.

DETAILED DESCRIPTION OF THE PREFERRED EMBODIMENT

Figure 1:
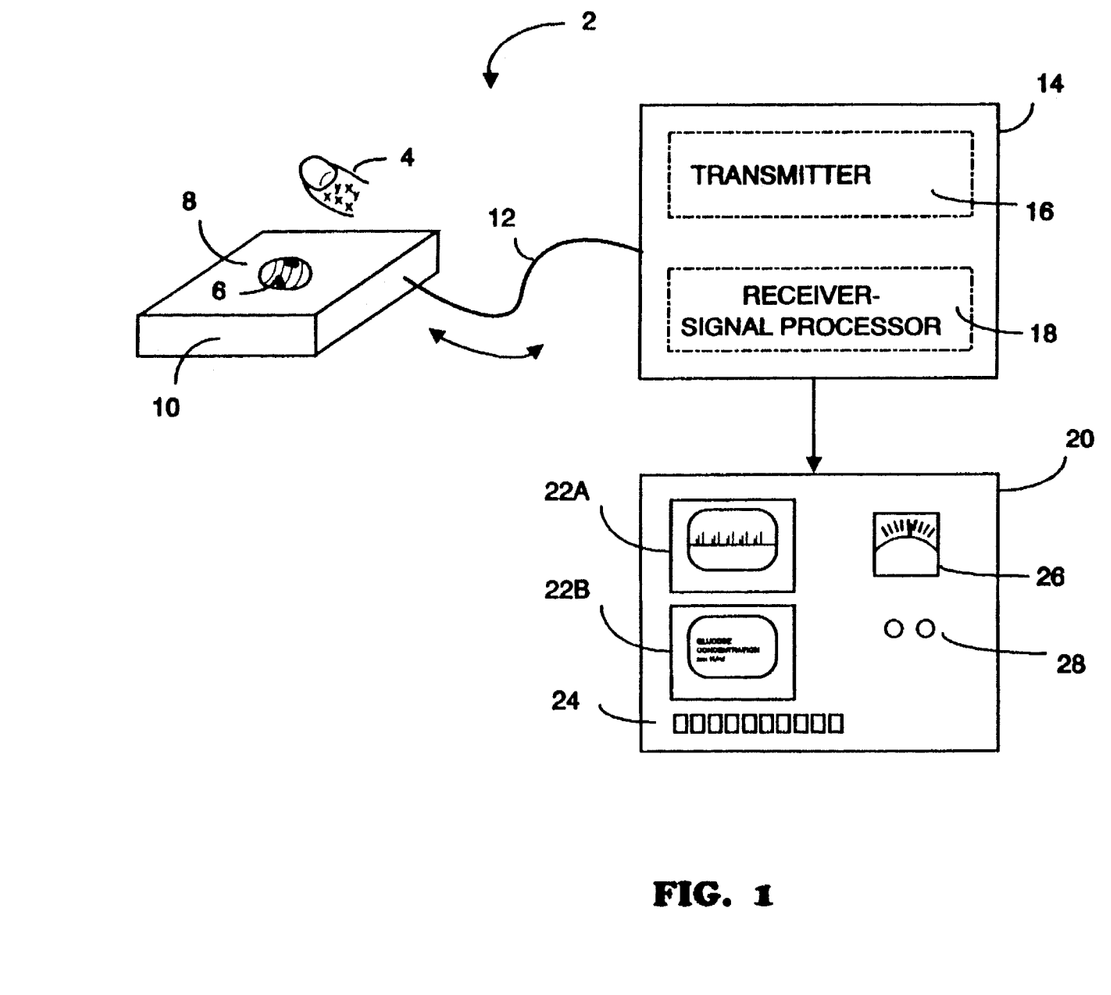
FIG. 1 is a block diagram of a radio frequency spectroscopy system according to the present invention.

FIG. 1 depicts a radio frequency ("RF") spectroscopy system 2, according to the present invention for determining the presence of one or more target chemicals (depicted as x, y) in a cell membrane specimen 4, e.g., a human finger. The specimen finger 4 is pressed against a probe pair 6, preferably disposed within a concave depression 8 formed in a lucite base 10. Probe pair 6 comprise two conductive rods that protrude slightly from the depression 8, permitting electrical contact to be made when finger 4 is pressed against the rods. Preferably the rods are brass, perhaps 0.2" (5 mm) outer diameter and protrude outward from the concave surface about 0.05" (1.3 mm), and into the lucite base about 0.5" (12 mm). Of course other tissue could be probed, e.g., an ear, and the specimen need not be a human.

A pair of transmission lines 12 electrically couples the electrode pair to a system 14 that includes a transmitter unit 16 and receiver-signal processor unit 18. Briefly, unit 16 transmits a high frequency signal via transmission lines 12 to probes 6, which couple the signal to the specimen finger 4. Although the precise mechanism is not fully understood, it appears that the presence of target chemicals, e.g., x and/or y, within the specimen may cause energy transfer of certain spectra of the source signal from transmitter 16. The result is that a return signal from the specimen, present at probe pair 6 and coupled via transmission lines 12 to unit 18, differs from the source signal. Of course separate probe units 6 could be used to couple the transmitter unit 16 to the specimen, and to couple the return signal from the specimen to unit 18.

Unit 18 receives and processes the return signal such that spectral signatures associated with the presence and concentration of various target chemicals within the specimen can be recognized. The processed data is then coupled to a display system 20 that conveys the detected information to a user. Operation of the receiver-signal processor unit 18 can be tailored, manually or automatically by a neural network, to recognize specific target chemicals, for example glucose within the blood stream within finger specimen 4. In such instance, the various output devices within display system 20 might provide a user with calibrated data as to his or her glucose concentration.

Display system 20 may include a monitor that can display a spectrum analyzer output (22A), and/or alphanumeric/graphical output (22B). Display system 20 may also include a bar graph or alpha-numeric indicator 24 indicating, for example, the concentration level of the target chemical, for example, glucose. A calibrated output meter 26 could provide the user with concentration data. Alternatively, a simple "GO/NO GO" output indicator 28 could alert the user that excess glucose concentration has been detected. A diabetic user would thus be alerted to take insulin immediately.

Figure 2:
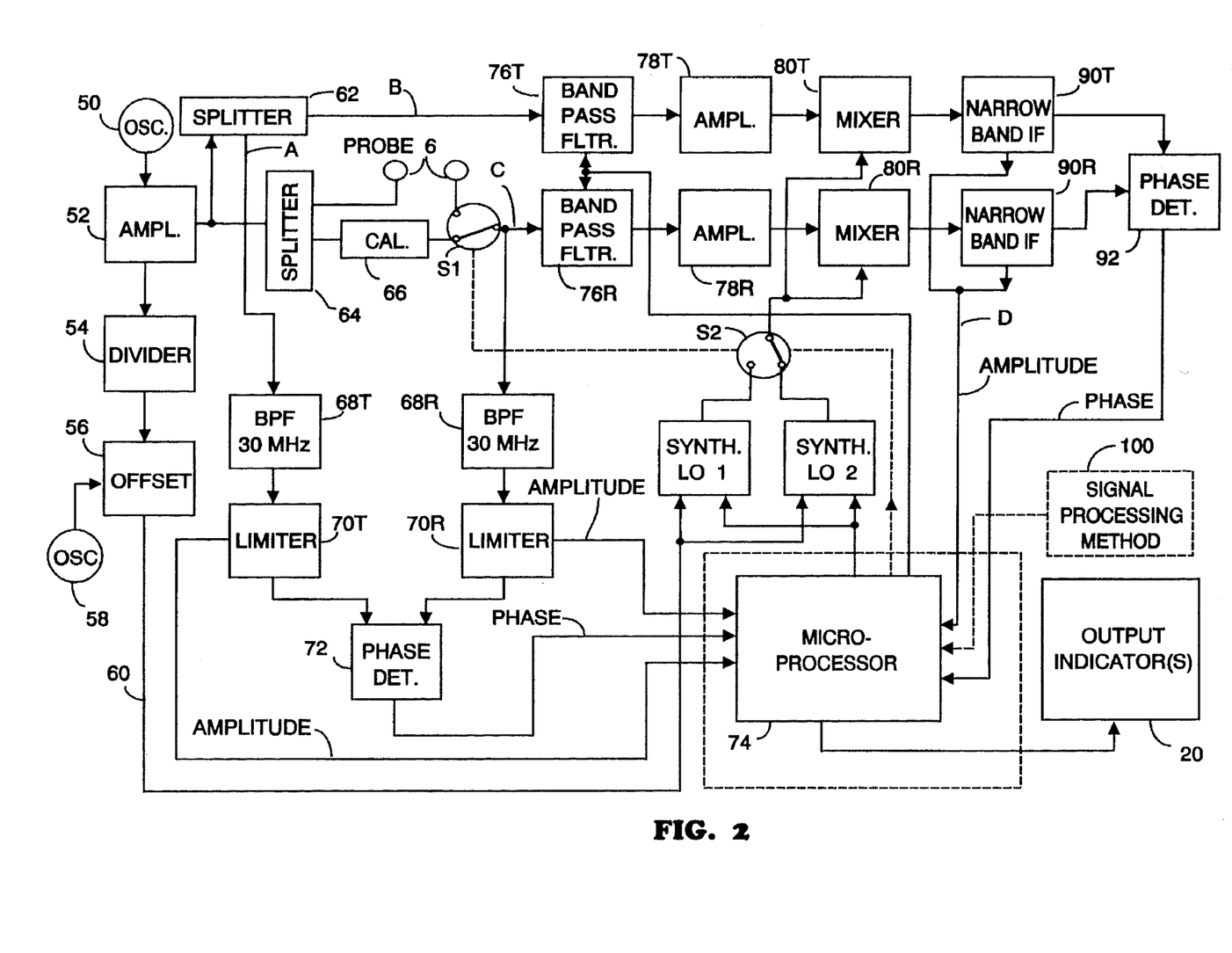
FIG. 2 is a block diagram of the transmitter/receiver-signal processing system 14, shown in FIG. 1, according to the present invention.

FIG. 2 is a block diagram of the transmitter/receiver-signal processing system 14. Oscillator 50 generates a high frequency stimulus signal that will be transmitted via probes 6 to specimen 4. In the preferred embodiment, oscillator 50 provides a 30 MHz fundamental square wave having a 50% duty cycle, and transition times of a few nanoseconds. As such, the oscillator output frequency spectrum will be rich in harmonics, the odd-numbered harmonics predominating. In the frequency domain, a perfect square-wave source signal would have harmonics with a sin(x)/x envelope, where x represents a harmonic frequency.

The spectral output of such an oscillator 50 is commonly referred to as a comb spectra, as the various spectra are uniformly spaced similar to the teeth on a comb. The power output level at the oscillator output is preferably about 1 mW, which is 0 dBm, although other power levels may also be used. In the preferred embodiment, the various source signal spectra are harmonically related since generation of a pulse train provides the harmonic frequencies automatically. However the source frequencies need not be harmonically related, and a single oscillator 50 may be rapidly changed between discrete frequencies (e.g., in the manner of spread spectrum transmitters). Alternatively, oscillator 50 could comprise a plurality of signal generators whose separate frequency outputs may or may not be harmonically related. If harmonically related, one such generator could provide a sinusoidal output at a fundamental frequency, e.g., 30 MHz. A second generator could provide a 60 MHz sinusoidal output, a third generator could provide a 90 MHz sinusoidal output, and so forth. In a different embodiment, one such generator might provide an output at frequency f1, a second generator might provide an output at f2, not harmonically related to f1, and so forth.

As used herein, oscillator 50 is understood to be a source of electromagnetic signal that contains a plurality of high frequency components, regardless of whether such components represent harmonics of a single source frequency, or represent many source frequencies, that need not be harmonically spaced-apart.

Unit 52 preferably includes an amplifier stage and a power splitter, and comprises a MAR-3 amplifier and a Cougar amplifier stage and a power splitter in the preferred embodiment. These commercially available components boost the oscillator signal provided to divider 54 to about 15 dBm, and provided to power splitters 62, 64 to about 3 dBm. In turn, each power splitter 62, 64 divides the thus amplified signal into two signals at nodes A and B, each having 0 dBm power output. Splitters 62, 64 are preferably wideband, e.g., about 10 MHz to 1,000 MHz (or 1 GHz). The intermediate frequency ("IF") for system 14 is preferably 21.4 MHz, an intermediate frequency commonly used in commercial equipment, for which frequency many standardized transformers and circuits are readily available. High-side mixing injection preferably is used. Thus, to generate a local oscillator frequency that is 21.4 MHz higher than a center frequency, it is necessary to develop a synthesized reference 6.4 MHz signal. Unit 54 divides the fundamental frequency of the oscillator signal by 6, to yield a nominal 5.0 MHz reference signal.

This 5.0 MHz reference signal and a 6.4 MHz phase-locked crystal controlled oscillator signal 58 are processed by offset module 56. Offset module 56 outputs on line 60 a signal having a frequency of 6.4 MHz that is phase locked to the 30 MHz frequency of oscillator 50. Because phase lock loop systems are well known in the art of digital signal processing design, further details of the generation of the frequency locked 6.4 MHz signal on line 60 are not presented here.

In FIG. 2, calibrator unit 66 is an electronic model of a typical human finger, essentially the electronic equivalent circuit of a finger specimen 4. While calibration unit 66 approximates the specimen impedance, unit 66 will not include the target chemical.

Figure 3A:
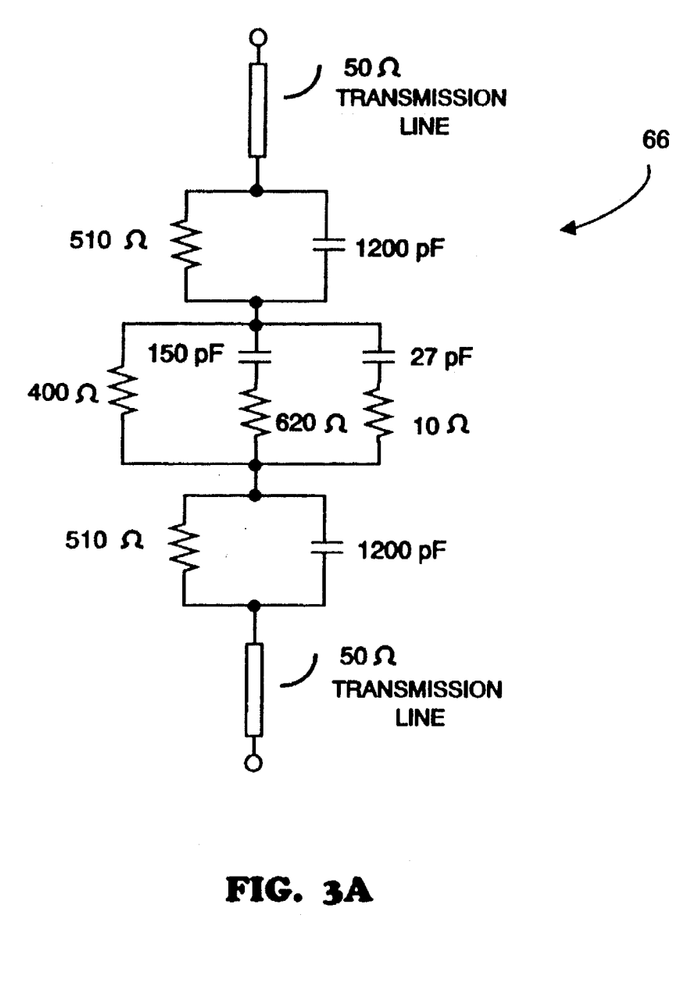
FIG. 3A is a schematic of the calibration cell 66, depicted in FIG. 2.
Figure 3B:
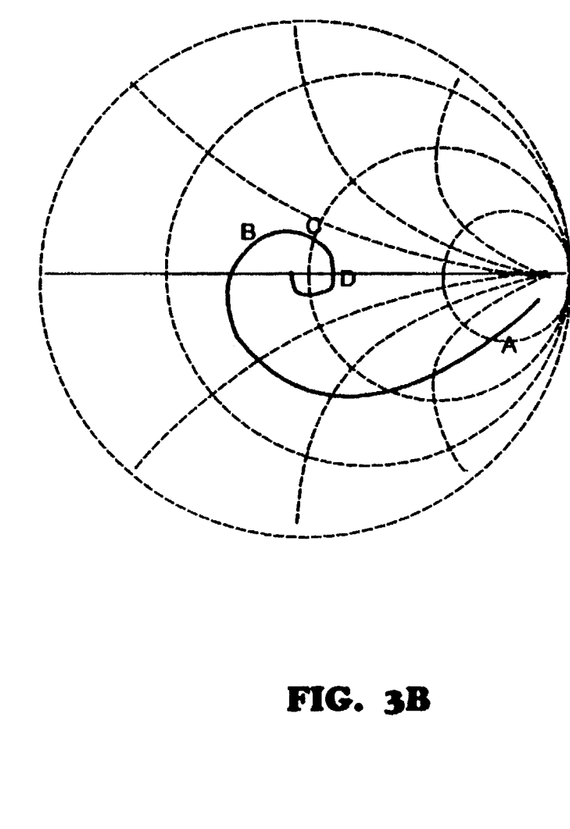
FIG. 3B is a Smith chart impedance versus frequency representation of the equivalent circuit depicted in FIG. 3A.

FIG. 3A details the circuitry within calibration unit 66, namely two segments of transmission line having 50 Ω impedance at 400 MHz, and assorted resistors and capacitors. The transmission lines, resistors and capacitors were selected empirically by comparing frequency versus impedance data from human fingers with data from the equivalent circuit of FIG. 3A. FIG. 3B is a Smith chart impedance versus frequency representation of the equivalent circuit of FIG. 3A. Point A in FIG. 3B represents an impedance of about 192 Ω/-201 Ω at 10 MHz, point B is 39.5 Ω/11.5 Ω at 300 MHz, C is 52 Ω at 400 MHz, and point D is about 57 Ω/-2.6 Ω at 500 MHz.

With further reference to FIG. 2, as will now be described, various components are replicated to provide a processing path for the transmitted source signal, and to provide a processing path for what will be termed the sampled return (or received) signal. The sampled return signal advantageously permits compensating the system of FIG. 2 for component variations and drift between what will be termed the received and the transmitted signal processing paths.

More specifically, the response of specimen 4 to the source signal (e.g., the return signal at the probe pair 6) is switchably sampled by switch S1 with the response of the calibration unit 66 to the source signal. Harmonic frequency-by-frequency, the output from probe pair 6 and from calibration unit 66 are sampled, the output of S1 providing a sampled return signal at node C to the remainder of system 18. Of course, if source oscillator 50 provided discrete frequencies that were not harmonically related, it is understood that frequency-by-frequency, the output from probe pair 6 and from calibration unit 66 would be sampled. In the preferred embodiment, the frequency bands of interest begin with about the sixth or seventh harmonic of source oscillator 50, e.g., about 195 MHz, and extend to about 1 GHz, or higher, which range is the bandwidth of system 18. Within that bandwidth, individual frequencies are sampled between probe pair 6 and calibration unit 66.

Switch S1 preferably is a commercially available monolithic microwave integrated circuit ("MMIC"), a relay, or other switching mechanism. S1 switches between the probe 6 output and the calibrator under control of a microprocessor 74 within system 14. In the preferred embodiment, microprocessor 74 was a Motorola 68HC11, although other microprocessors could be used instead.

S1 may sample the output of probe 6 for a time period ranging from perhaps 30 ms to perhaps 7 seconds, and then may sample the output of the calibration unit 66 for a time period also within that range, the duty cycle typically being aperiodic. For example, during the time S1 is coupled to probe 6, the probe output signal is sampled for one or more frequencies that are harmonics of the fundamental frequency of oscillator 50 (or for one or more discrete frequencies provided by an oscillator 50 that does not provide harmonics). During the time S1 is coupled to the calibration unit 66, the response of calibration unit 66 to one or more frequencies that are harmonics of the fundamental oscillator 50 frequency are sampled.

Understandably, if components 76T and 76R, 78T and 78R, 80T, 80R, 90T and 90R (to be described) were identical and exhibited no drift, calibration unit 66 could be dispensed with, and S1 replaced by a wire making a permanent connection in the probe 6 S1 position. Such an ideal system would require no mechanism for compensating for drift and other differences in the signal processing paths for the harmonics of the oscillator signal 50, and for the harmonics in the return signal obtained from probe 6.

In practice, variations in temperature and/or pressure between probe pair 6 and the tissue in the specimen 4 may contribute some error to the measurement process. To permit microprocessor 74 to compensate for such error, in addition to providing the microprocessor with phase and amplitude information for harmonics, the present invention also provides phase and amplitude information for the oscillator fundamental frequency. This frequency has been found experimentally to be sensitive to such temperature and/or pressure variations. It is understood that suitable temperature and/or pressure transducers and analog-to-digital conversion components that are not shown in FIG. 1 are used.

As shown in FIG. 2, within the transmitted source signal processing path, a bandpass filter 68T has a center frequency equal to that of oscillator 50, e.g., 30 MHz, and a bandwidth of about 1 KHz to perhaps 1 MHz. Other bandwidths could be used and in fact, a 30 MHz lowpass filter might instead be used. The transmitted signal from node A is coupled to bandpass filter 68T, and the 30 MHz center frequency component of this signal passes from filter 68T and is amplitude limited by limiter 70T. The thus bandpass filtered and amplitude limited signal is coupled to an input of a phase detector 72.

In a parallel path, the sampled return signal from switch S1, present at node C, passes through a similar 30 MHz bandpass filter 68R, amplitude limiter 70R to provide a second input to phase detector 72. (The letter T or R attached to a reference element herein denotes that the element is used in the transmitted source path, e.g., 68T, or is used in the sampled return signal path, e.g., 68R.)

Phase detector 72 compares the difference in phase between the transmitted 30 MHz fundamental frequency and the sampled return 30 MHz fundamental frequency signal. The phase detector 72 output signal voltage will be proportional to such phase shift, e.g., a number of mV per each degree of phase shift. As shown in FIG. 2, the phase output information from detector 72 is coupled to microprocessor 74 for analysis. Proceeding horizontally across the top of FIG. 2, parallel paths are also depicted for processing the transmitted source signal harmonics (available at node B) and the sampled return signal harmonics from switch S1 (available at node C). These two horizontal paths use substantially identical components (as denoted by the nomenclature) to provide transmitted and sampled return signals at an intermediate frequency (IF) that is about 21.4 MHz in the preferred embodiment.

Briefly, the components now to be described resolve the harmonic frequency components of the signals at node B and node C into preferably four bands of discrete frequencies, depending upon what harmonics of the source oscillator signals are desired to be examined.

Much of the remainder of the signal processor functions as a scanner-receiver, that under microprocessor control scans discrete harmonic frequencies of interest. The transmitted source signal path components will first be described, it being understood that identical components are used in the parallel sampled return signal path, as indicated by the nomenclature, e.g., 76T, 76R, 78T, 78R, etc. Bandpass filter 76T (and thus also 76R) preferably is a filter bank that includes an internal MMIC switching mechanism operating under control of microprocessor 74. The input port of filter 76T passes the transmitted signal from node B through an internal switch into two banks of pre-shaping three-pole bandpass filters. These first two internal filter banks have bandpasses of 195 MHz to 395 MHz, and 395 MHz to 805 MHz. Still within filter bank 76T, the outputs from the 195–395 MHz and 395–805 MHz filters pass through additional internal MMIC switches and bandpass filters. These additional filters pass 195–295 MHz, 295–405 MHz, 405–610 MHz, and 605–815 MHz. Still within 76T, the variously filtered components are combined into a single signal that is amplified by amplifier 78T.

In similar fashion, the sampled return signal at node C is passed through switching bandpass filters within bandpass filter bank 76R, and the variously filtered components are combined and amplified by amplifier 78R. While the operation of bandpass filter banks 76T, 76R has been described with reference to specific frequency bands, those skilled in the art will recognize that the frequencies comprising the signals at nodes B and C may be filtered using bandpass filters having different ranges of bandpass. Because the design of units 76T, 76R is known to those skilled in the relevant art, schematics are not here provided.

For example, if the target chemical of interest is best resolved by examining say the seventh harmonic of the 30 MHz transmitted source signal (or a given discrete frequency of a source signal providing a plurality of frequencies not necessarily harmonically related), microprocessor 74 is caused to control the switching within units 76T, 76R to pass 210 MHz frequency components, e.g., to select the 195 MHz–295 MHz bandpass. Amplifiers 78T, 78R preferably have sufficient gain to compensate for attenuation caused by filters 76T, 76R, and have a bandwidth of at least 195 MHz to 815 MHz.

Of course, if amplifiers 78T, 78R were ideal and not subject to front-end overload, it would be possible to delete the bandpass filter systems 76T, 76R, and rely upon the operation of mixers 80T, 80R, and narrow band IF units 90T, 90R (to be described), to separate the various harmonic components of the oscillator signal and of the return signal.

As shown by FIG. 2, the output signals from amplifiers 78T, 78R are provided as an input signal to mixers 80T, 80R. Frequency synthesized local oscillators LO1 or LO2 provide respective second input signals to mixers 80T, 80R, via a MMIC switch $2 (or similar device) that switches between the two synthesized oscillator signals under control of microprocessor 74.

The synthesized LO1 or LO2 signals are then frequency mixed against the selective spectral components of the transmitted source signal and sampled return signal that have been switchably selected to pass through filter banks 76T, 76R. The LO1 or LO2 output signals are 21.4 MHz above the harmonic frequency of interest. Because of the difficulty associated with implementing a synthesized local oscillator whose output frequency can range from about 231.4 MHZ (e.g., 7×30 MHz+21.4 MHz) to perhaps 800 Mhz (e.g., about the twenty-sixth harmonic 26×30 MHz 21.4 MHz), the preferred embodiment employed two local oscillators, LO1, LO2. If, however a suitable synthesized oscillator having a two-octave frequency output could be implemented, such oscillator would replace LO1, LO2 and the necessity for S2.

Stages 90T, 90R are narrowband intermediate frequency circuits that pass a 21.4 MHz center frequency with a bandwidth of about 25 KHz. Of course by suitably offsetting mixing frequencies, an IF of other than 21.4 MHz could be used. In the preferred embodiment, IF units 90T, 90R are similar to IF units commonly found in commercially available cellular telephones.

The harmonic frequency information passing through IF units 90T and 90R are input to phase detector 92. Phase detector 92 compares transmitted source and sampled return signals at each harmonic frequency of interest. The difference in phase between these signals is then provided by phase detector 92 to microprocessor 74. At the same time, the relative voltage levels from the IF units 90T, 90R at node D are also provided (after suitable analog to digital conversion, converter not shown) to microprocessor 74.

To recapitulate, microprocessor 74 receives phase information from detector 92 that is relative to the various harmonics of the source signal (or discrete frequencies of interest if a non-harmonic generator 50 is employed), and that is relative to the various harmonics (or discrete frequencies) of the source signal as altered by the target substance and received at the probe pair 6. Similarly, microprocessor 74 receives amplitude information of IF units 90T and 90R relative to the various harmonics (or discrete frequencies of interest) of the source signal, and that is relative to the various harmonics (or discrete frequencies) of the source signal as altered by the target substance and received at probe pair 6. Further, to permit compensation for probe temperature and/or probe-specimen pressure variations, limiters 70T, 70R provide microprocessor 74 with amplitude of the source frequency, and with amplitude of the source frequency as altered by the target substance and received at probe pair 6, while detector 72 provides similar phase information for the source frequency.

Microprocessor 74 operates under program control, generating data for further processing by a so-called neural network, look-up table, algorithm, or other method of signal processing, shown symbolically in FIG. 2 as element 100. In a manner known to those skilled in the relevant art, a neural network 100 can be "trained" to recognize a spectral signature associated with a given target chemical, glucose for example. To ease this recognition, neural network 100 can optimize the manner of signal processing within unit 14.

For example, the operation of filter banks 76T, 76R can be altered under control of microprocessor 74. In a more generalized embodiment, the number and bandwidth of individual bandpass filters within units 76T, 76R could be dynamically modified by suitable MMIC-selection, all under microprocessor control. However, unit 100 may simply be a look-up table, correlating relative amplitude changes in a return signal with harmonic frequency against presence or concentration of a target chemical in the specimen. Further, a suitable neural network 100 might control microprocessor 74 to optimize the generation of discrete frequencies, based upon processed signature data. For example, if a certain set of frequencies from oscillator 50 provided a slight spectral signature, network 100 might direct oscillator 50 to provide slightly different frequencies until the signature was more recognizable.

Microprocessor 74 in turn provides output signals to output indicator(s) 20. As has been described, output indicator(s) 20 can, in a variety of formats, display information enabling a user to determine the presence and concentration of a desired target chemical (e.g., x) in a specimen. In the preferred embodiment, the specimen is in fact a finger of the individual using the present invention. While the present invention has been implemented in breadboard fashion, those skilled in the art will appreciate that it may in fact be fabricated in a handheld, battery operated, portable unit. In such embodiment, output indicator(s) 20 would preferably include liquid crystal displays (LCDs) or simple GO/NO GO indicators, to preserve power and space. Preferably base 10 would be attached to the case housing the remainder of the present invention, for ease of portability.

Figure 4A:
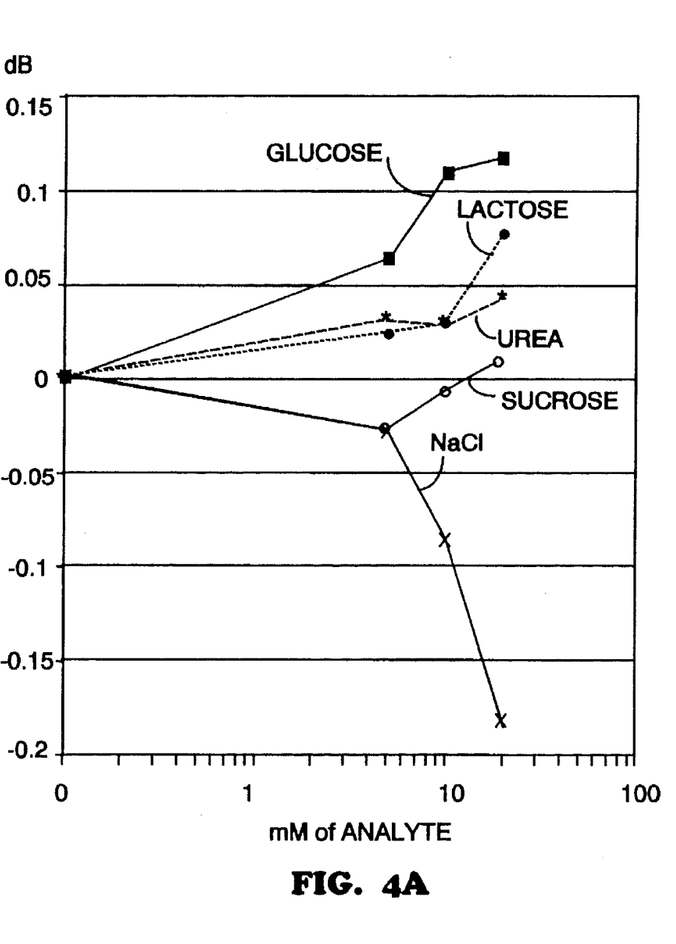
FIGS. 4A, 4B, and 4C depict signal amplitudes provided by the present invention for different target chemicals in analyte test solutions.
Figure 4B:
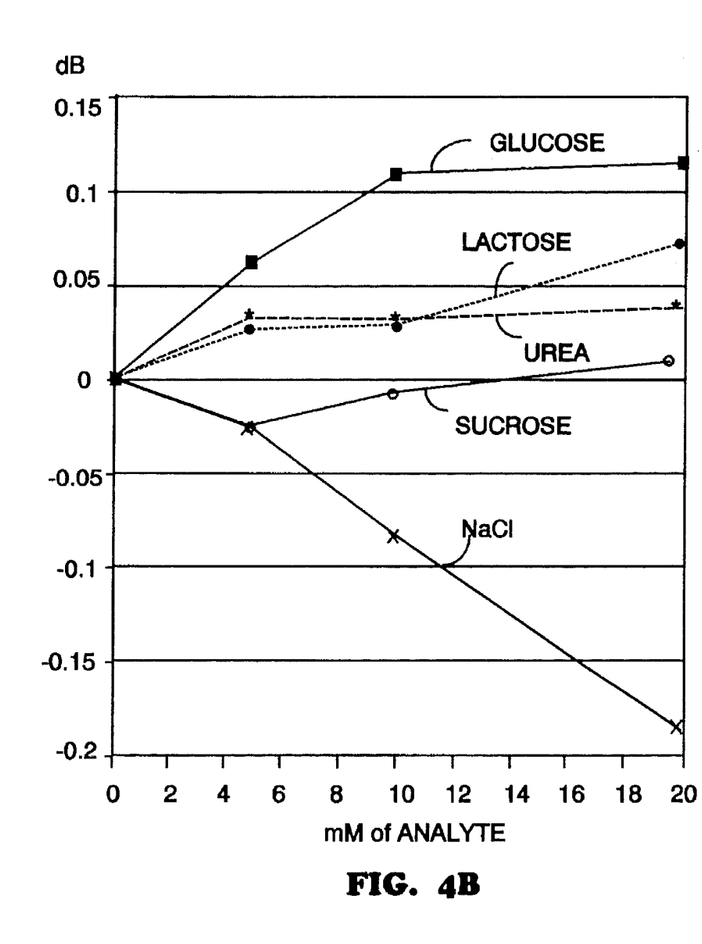
Figure 4C:
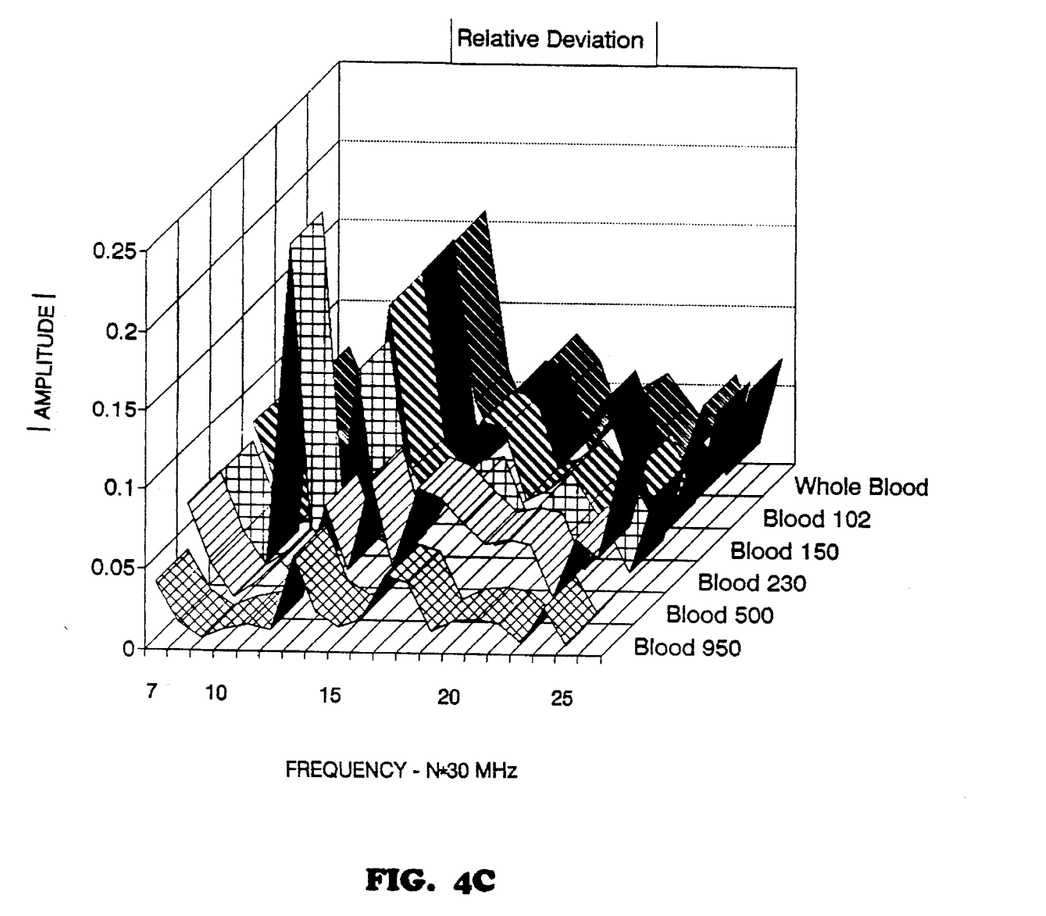

FIGS. 4A and 4B represent multiple averaged in-vitro data obtained with the present invention, using as a test specimen whole blood (e.g., red blood cells) to which glucose or lactose or sucrose or urea or NaCl was added as a test chemical. The test cells were compared to a calibrated cell that contained only red blood cells. FIG. 4C represents similar data for whole sheep's blood (e.g., no glucose), and for sheep's blood with various concentrations of glucose, where the nomenclature "Blood 102" denotes 102 mg-% or 102 mg per dL glucose. Typically, a healthy human has perhaps 80–120 mg% glucose, while a diabetic has 200–400 mg-% glucose. The vertical axis in FIG. 4C represents the vector amplitude the return signal, taking into account magnitude and phase. The horizontal axis represents harmonics of a 30 MHz source frequency, the first harmonic being at 210 MHz.

To minimize probe-related variables, the specimens in FIGS. 4A, 4B and 4C were tested using parallel plate capacitive cells. These cells comprised two dielectric substrates having a relative permittivity approximating that of water ($\approx 80$), with an electrode surface baked onto each substrate. The test substance was placed in a chamber between the substrates.

The varying degree of signal amplitude shown in FIGS. 4A, 4B, and 4B are termed "spectral signatures". What is depicted is the difference in amplitude between the calibrated cell (analogous to the use of the calibration unit 66 in FIG. 2) and the test specimen (analogous to the use of probes 6 and specimen 4 in FIG. 1). These data indicate that the present invention may be used to discern the presence of a target chemical within a test specimen or sample.

A preferred use of the present invention is the detection of excess glucose in a user's blood, e.g., within the specimen. Because the present invention operates non-invasively, it suffices for the user to press his or her finger against the probe pair 6, as shown in FIG. 1. In response to the high frequency, high harmonic content signal from transmitter 16, chemicals within the specimen can recognizably cause energy transfer of certain spectral components of the transmitted source signal. It is hypothesized that within the specimen, the target chemical glucose interacts with the lipid bilayer and/or red blood cell membranes.

Thus, in the presence of frequency components from the signal transmitted via probes 6, the glucose seems to bring about non-linear intermodulation or mixing of frequency components, possibly due to a non-linear dielectric phenomenon involving capacitance associated with glucose. With the present invention, a diabetic user may rapidly obtain glucose concentration level information. Signal processing by unit 18 would, essentially in real time, provide glucose level information on display unit 20.

Of course other target chemicals may also be detected, including for example fructose, galactose, alcohol. For example, a system according to the present invention may be used to sense alcohol in a motorist's system, either by a motorist before attempting to drive, or by a police officer attempting to determine whether an individual is under the influence of alcohol.

Because the present invention appears to be sensitive to boundary conditions at a lipid bilayer membrane, disruptions to such boundary conditions may be detected by a spectral signature. Thus, the presence of glucose in varying amounts at a membrane may be detected according to the present invention.

In a different utility, however, trauma to a specimen that interferes with such boundary conditions may also be detected, primarily for the purpose of providing medical treatment. For example victims of electrocution may received localized injuries, for example on an arm. Unless the injury sites are promptly treated by the injection of certain medication that is potentially rather toxic, the victim will lose the injured limb or die. Use of the present invention would permit diagnosis of such injury sites, and quantizing the injury to facilitate prompt and accurate medical treatment.

Modifications and variations may be made to the disclosed embodiments without departing from the subject and spirit of the invention as defined by the following claims.

What is claimed is:

1. A non-invasive method for determining concentration of at least one target chemical in a specimen, the method comprising the following steps:

(a) coupling to a specimen a source electromagnetic signal containing simultaneously at least first and second frequency components that are each at least 30 MHz and include harmonics that do not exceed about 1 GHz;

(b) receiving from said specimen at least two spectral components in a return signal;

(c) processing said received at least two spectral components to produce a spectral signature having frequency-identifiable spectral components therein; and (d) determining a concentration of at least one target chemical in said specimen based upon said spectral signature.

2. The method of claim 1, wherein step (a) includes coupling a source electromagnetic signal having at least one characteristic selected from the group consisting of: (i) a fundamental frequency of about 30 MHz, (ii) rise and fall transition times less than about 10 ns, (iii) a duty cycle of about 50%, (iv) a power level in the range of about 0 dBm to +10 dBm, (v) said signal includes at least one spectral component promoting exchange of energy in the presence of a said target chemical in said specimen, (vi) said signal is generated from a plurality of signal sources, and (vii) said plurality of frequency components are not all harmonically related.

3. The method of claim 1, wherein said specimen has at least one characteristic selected from the group consisting of (i) said specimen includes a cell membrane, (ii) said specimen is living tissue, (iii) said specimen is human tissue, and (iv) said specimen is a human finger.

4. The method of claim 1, wherein said specimen is human tissue, and steps (a) and (b) include coupling to and receiving from said specimen via a probe pair placed in contact with a portion of said specimen.

5. The method of claim 1, wherein at least one target chemical includes at least one chemical selected from the group consisting of (i) glucoses, (ii) lactose, (iii) urea, (iv) sucrose, (v) NaCl, (vi) fructose, (vii) galactose, and (viii) an alcohol.

6. The method of claim 1, wherein at least some of said plurality of frequency components are harmonically related, and wherein step (c) includes comparing at least two harmonics of said source electromagnetic signal with said at least two harmonics of said source electromagnetic signal as are present in said return signal.

7. The method of claim 1, wherein said source electromagnetic signal has a fundamental frequency of about 30 MHz and includes harmonics thereof, and wherein step (c) includes comparing N harmonics of said 30 MHz signal with said N harmonics of said 30 MHz signal as are present in said return signal, where N is an integer $\geq 2$.

8. The method of claim 1, wherein step (c) includes passing said received at least two spectral components through a bank of filters having at least one characteristic selected from the group consisting of (i) said bank includes at least two switchably selected bandpass filters whose passband passes a chosen frequency component of said source electromagnetic signal, and (ii) said bank resolves said received at least two spectral components into a plurality of bandpass regions each region being at least 100 MHz wide.

9. The method of claim 1, wherein step (c) includes the step of forming a sampled return signal from the response of said source electromagnetic signal of a calibration circuit, and from the response of said source electromagnetic signal to said specimen.

10. The method of claim 9, wherein step (c) includes the step of comparing frequency components present in said sampled return signal with frequency components present in said source electromagnetic signal.

11. The method of claim 4, wherein step (c) includes the additional step of correcting for environmental error associated with said probe pair, said environmental error including at least one component selected from the group consisting of temperature error and pressure error of said probe pair against said specimen.

12. The method of claim 11, wherein said additional step of correcting includes comparing a fundamental frequency of said return signal with a fundamental frequency of said source electromagnetic signal.

13. The method of claim 9, wherein step (c) includes digital signal processing said sampled return signal and said source electromagnetic signal, said digital signal processing occurring under control of a microprocessor.

14. The method of claim 1, wherein step (d) includes correlating a concentration of said target chemical associated with said spectral signature with a concentration level of said target chemical known to represent a relational value, said step of correlating employing at least one element selected from the group consisting of (i) a look-up table, (ii) a neural network, and (iii) an algorithm.

15. The method of claim 1, further including the step of optimizing said processing step (c) and said determining step (d) with a neutral network.

16. The method of claim 1, further including the step of displaying information associated with said concentration of said target chemical so correlated.

17. An apparatus for non-invasively determining concentration of at least one target chemical in a specimen, comprising:

(a) means for providing a source electromagnetic signal containing simultaneously at least first and second frequency components that are each at least about 30 MHz and include harmonica that do not exceed about 1 GHz;

(b) means for coupling said source electromagnetic signal to a specimen;

(c) means for receiving from said specimen at least two spectral components in a return signal;

(d) means for processing said received at least two spectral components to produce a spectral signature having frequency-identifiable spectral components therein; and (e) means for determining a concentration of at least one target chemical in said specimen based upon said spectral signature.

18. The apparatus of claim 17, wherein said means for providing includes a transmitter whose source electromagnetic signal has at least one characteristic selected from the group consisting of: (i) a fundamental frequency of about 30 MHz, (ii) rise and fall transition times less than about 10 ns, (iii) a duty cycle of about 50%, (iv) a power level in the range of about 0 dBm to +10 dBm, (v) said signal includes at least one spectral component promoting exchange of energy in the presence of a said target chemical in said specimen, (vi) said signal is generated from a plurality of signal sources, and (vii) said plurality of frequency components are not all harmonically related.

19. The apparatus of claim 17, wherein said specimen has at least one characteristic selected from the group consisting of (i) said specimen includes a cell membrane, (ii) said specimen is living tissue, (iii) said specimen is human tissue, and (iv) said specimen is a human finger.

20. The apparatus of claim 17, wherein said specimen is human tissue, and said means for receiving and said means for processing include a common probe pair, placed in contact with a portion of said specimen, said common probe pair being coupled to said means for receiving and to said means for processing.

21. The apparatus of claim 17, wherein said a target chemical includes at least one chemical selected from the group consisting of (i) glucose, (ii) lactose, (iii) urea, (iv) sucrose, (v) NaCl, (vi) fructose, (vii) galactose, and (viii) an alcohol.

22. The apparatus of claim 17, wherein said plurality of frequency components includes components that are harmonically related, and wherein said means for processing compares at least two harmonics of said source electromagnetic signal with said at least two harmonics of said source electromagnetic signal as are present in said return signal.

23. The apparatus of claim 17, wherein said source electromagnetic signal has a fundamental frequency of about 30 MHz and includes harmonics thereof, and wherein said means for processing compares N harmonics of said 30 MHz signal with said N harmonics of said 30 MHz signal as are present in said return signal, where N is an integer $\geq 2$.

24. The apparatus of claim 17, wherein said means for processing passes said received at least two spectral components through a bank of filters having at least one characteristic selected from the group consisting of (i) said bank includes at least two switchably selected bandpass filters whose passband passes a chosen frequency component of said source electromagnetic signal; and (ii) said bank resolves said received at least two spectral components into a plurality of bandpass regions each region being at least 100 MHz wide.

25. The apparatus of claim 17, wherein said means for processing forms a sampled return signal from the response of said source electromagnetic signal of a calibration circuit, and from the response of said source electromagnetic signal to said specimen.

26. The apparatus of claim 17, wherein said means for processing compares frequency components present in said sampled return signal with frequency components present in said source electromagnetic signal.

27. The apparatus of claim 20, further including means for correcting for environmental error associated with said probe pair, said environmental error including at least one component selected from the group consisting of temperature error and pressure error of said probe pair against said specimen.

28. The apparatus of claim 27, wherein said means for correcting compares a fundamental frequency of said return signal with a fundamental frequency of said source electromagnetic signal.

29. The apparatus of claim 25, wherein said means for processing digitally signal processes said sampled return signal and said source electromagnetic signal, said digital signal processing occurring under control of a microprocessor.

30. The apparatus of claim 17, wherein said means for correlating correlates a concentration of said target chemical associated with said spectral signature with a concentration level of said target chemical known to represent a relational value, said means for correlating employing at least one element selected from the group consisting of (i) a look-up table, (ii) a neural network, and (iii) an algorithm.

31. The apparatus of claim 17, further including neural network means for optimizing operations of said means for processing and said means for correlating.

32. The apparatus of claim 17, further including means for displaying information associated with said concentration of said target chemical so correlated.

* * * * *